US012053323B2

United States Patent
Fife et al.

(10) Patent No.: US 12,053,323 B2
(45) Date of Patent: Aug. 6, 2024

(54) PRESSURE PORT FOR ULTRASONIC TRANSDUCER ON CMOS SENSOR

(71) Applicant: BFLY Operations, Inc., Guilford, CT (US)

(72) Inventors: Keith G. Fife, Palo Alto, CA (US); Jianwei Liu, Fremont, CA (US); Jungwook Yang, Newton, MA (US); Joseph Lutsky, Los Altos, CA (US)

(73) Assignee: BFLY Operations Inc, Guilford, CT (US)

( * ) Notice: Subject to any disclaimer, the term of this patent is extended or adjusted under 35 U.S.C. 154(b) by 383 days.

(21) Appl. No.: 16/401,870

(22) Filed: May 2, 2019

(65) Prior Publication Data

US 2019/0336099 A1 Nov. 7, 2019

Related U.S. Application Data

(60) Provisional application No. 62/696,305, filed on Jul. 10, 2018, provisional application No. 62/666,556, filed on May 3, 2018.

(51) Int. Cl.
*A61B 8/12* (2006.01)
*B06B 1/02* (2006.01)
(Continued)

(52) U.S. Cl.
CPC .............. *A61B 8/12* (2013.01); *B06B 1/0207* (2013.01); *B06B 1/0292* (2013.01);
(Continued)

(58) Field of Classification Search
None
See application file for complete search history.

(56) References Cited

U.S. PATENT DOCUMENTS 4,262,399 A * 4/1981 Cady ..................... B06B 1/0292
257/416
5,311,095 A * 5/1994 Smith ..................... B06B 1/064
310/334
(Continued)

FOREIGN PATENT DOCUMENTS

CN 106659464 A 5/2017
EP 0389071 A2 * 9/1990 ........... G01L 9/0042
(Continued)

OTHER PUBLICATIONS

Adelegan, Oluwafemi J., et al. "Fabrication of 32× 32 2D Capacitive Micromachined Ultrasonic Transducer (CMUT) Arrays on a Borosilicate Glass Substrate With Silicon-Through-Wafer Interconnects Using Sacrificial Release Process." Journal of Microelectromechanical Systems 30.6 (2021): 968-979. (Year: 2021).*
(Continued)

*Primary Examiner* — Isam A Alsomiri
*Assistant Examiner* — Jonathan D Armstrong
(74) *Attorney, Agent, or Firm* — Boston & Galway, LLC

(57) ABSTRACT

Micromachined ultrasonic transducers having pressure ports are described. The micromachined ultrasonic transducers may comprise flexible membranes configured to vibrate over a cavity. The cavity may be sealed, in some instances by the membrane itself. A pressure port may provide access to the cavity, and thus control of the cavity pressure. In some embodiments, an ultrasound device including an array of micromachined ultrasonic transducers is provided, with pressure ports for at least some of the ultrasonic transducers. The pressure ports may be used to control pressure across the array.

16 Claims, 12 Drawing Sheets

(51) Int. Cl.
  *B06B 1/06* (2006.01)
  *G01N 29/24* (2006.01)
  *H10N 30/20* (2023.01)

(52) U.S. Cl.
  CPC ........ *B06B 1/0622* (2013.01); *G01N 29/2406* (2013.01); *H10N 30/204* (2023.02)

(56) References Cited

U.S. PATENT DOCUMENTS

| | | | | |
|---|---|---|---|---|
| 5,619,476 | A * | 4/1997 | Haller | B06B 1/0292 367/153 |
| 5,639,423 | A * | 6/1997 | Northrup | B01F 11/0266 422/50 |
| 5,744,898 | A * | 4/1998 | Smith | B06B 1/064 310/334 |
| 5,870,351 | A * | 2/1999 | Ladabaum | B06B 1/0292 367/163 |
| 5,894,452 | A * | 4/1999 | Ladabaum | B06B 1/0292 381/174 |
| 5,982,709 | A * | 11/1999 | Ladabaum | H01L 41/0973 381/174 |
| 6,262,946 | B1 * | 7/2001 | Khuri-Yakub | B06B 1/0292 367/153 |
| 6,271,620 | B1 * | 8/2001 | Ladabaum | B06B 1/0292 310/334 |
| 6,278,224 | B1 * | 8/2001 | Sawada | B06B 1/0622 310/334 |
| 6,323,580 | B1 * | 11/2001 | Bernstein | H01L 27/20 310/324 |
| 6,328,697 | B1 * | 12/2001 | Fraser | B06B 1/0292 600/459 |
| 6,430,109 | B1 * | 8/2002 | Khuri-Yakub | B06B 1/0292 367/181 |
| 6,891,711 | B1 * | 5/2005 | Kurtz | H01G 5/16 361/290 |
| 7,616,077 | B1 * | 11/2009 | Wittwer | H03H 3/0072 333/186 |
| 7,940,603 | B2 | 5/2011 | Hideo et al. | |
| 8,324,006 | B1 * | 12/2012 | Adler | B06B 1/0292 438/50 |
| 9,061,318 | B2 | 6/2015 | Rothberg et al. | |
| 9,067,779 | B1 | 6/2015 | Rothberg et al. | |
| 9,242,275 | B2 | 1/2016 | Rothberg et al. | |
| 9,351,706 | B2 | 5/2016 | Rothberg et al. | |
| 9,420,378 | B1 * | 8/2016 | Syed | H04R 19/04 |
| 9,439,000 | B1 * | 9/2016 | Daley | H04R 7/16 |
| 9,499,392 | B2 | 11/2016 | Rothberg et al. | |
| 9,505,030 | B2 | 11/2016 | Rothberg et al. | |
| 9,521,991 | B2 | 12/2016 | Rothberg et al. | |
| 9,533,873 | B2 | 1/2017 | Rothberg et al. | |
| 9,592,030 | B2 | 3/2017 | Rothberg et al. | |
| 9,778,348 | B1 | 10/2017 | Chen et al. | |
| 10,082,565 | B2 | 9/2018 | Chen et al. | |
| 10,175,347 | B2 | 1/2019 | Chen et al. | |
| 10,187,020 | B2 | 1/2019 | Chen et al. | |
| 10,189,049 | B2 * | 1/2019 | Torashima | G01N 29/2418 |
| 10,196,261 | B2 | 2/2019 | Rothberg et al. | |
| 10,231,713 | B2 | 3/2019 | Chen et al. | |
| 10,293,374 | B2 * | 5/2019 | Torashima | G01N 29/2418 |
| 10,497,856 | B2 | 12/2019 | Rothberg et al. | |
| 10,512,936 | B2 | 12/2019 | Alie et al. | |
| 10,583,462 | B2 * | 3/2020 | Torashima | B06B 1/0292 |
| 10,850,306 | B2 | 12/2020 | Rothberg et al. | |
| 10,856,840 | B2 | 12/2020 | Rothberg et al. | |
| 10,856,844 | B2 | 12/2020 | Fife et al. | |
| 10,972,842 | B2 | 4/2021 | Lutsky et al. | |
| 11,018,068 | B2 | 5/2021 | Liu et al. | |
| 2002/0083771 | A1 * | 7/2002 | Khuri-Yakub | G01N 29/222 73/589 |
| 2006/0163680 | A1 * | 7/2006 | Chen | A61M 37/00 257/416 |
| 2008/0089181 | A1 | 4/2008 | Adachi et al. | |
| 2010/0168583 | A1 * | 7/2010 | Dausch | A61B 8/4488 600/466 |
| 2010/0207484 | A1 * | 8/2010 | Chang | B06B 1/0292 310/300 |
| 2010/0327695 | A1 * | 12/2010 | Goel | B06B 1/0622 310/320 |
| 2011/0036808 | A1 * | 2/2011 | Matsumoto | B06B 1/0292 216/17 |
| 2011/0055447 | A1 | 3/2011 | Costa | |
| 2011/0073968 | A1 * | 3/2011 | Ezaki | H01L 27/1203 257/416 |
| 2011/0095645 | A1 * | 4/2011 | Chang | B06B 1/0292 310/300 |
| 2011/0115337 | A1 * | 5/2011 | Nakamura | G10K 9/122 310/334 |
| 2011/0120971 | A1 * | 5/2011 | Martin | B81C 1/00904 216/41 |
| 2011/0260576 | A1 * | 10/2011 | Masaki | H04R 31/00 310/300 |
| 2011/0316054 | A1 | 12/2011 | Fedder et al. | |
| 2011/0316383 | A1 * | 12/2011 | Machida | B81C 1/00611 310/300 |
| 2012/0086087 | A1 | 4/2012 | Fitzpatrick | |
| 2012/0112603 | A1 * | 5/2012 | Masaki | B81C 1/00047 310/308 |
| 2012/0256518 | A1 * | 10/2012 | Torashima | B06B 1/0292 310/300 |
| 2012/0256519 | A1 * | 10/2012 | Tomiyoshi | H04R 1/00 310/300 |
| 2012/0256520 | A1 * | 10/2012 | Torashima | H02N 1/08 310/300 |
| 2014/0313861 | A1 * | 10/2014 | Torashima | H04R 19/00 367/181 |
| 2014/0332911 | A1 * | 11/2014 | Dirksen | B06B 1/0292 257/416 |
| 2014/0375168 | A1 * | 12/2014 | Dirksen | H02N 1/08 310/300 |
| 2015/0107360 | A1 * | 4/2015 | Akiyama | G01H 9/008 73/632 |
| 2015/0135841 | A1 * | 5/2015 | Kato | B81B 3/0021 73/655 |
| 2015/0165479 | A1 * | 6/2015 | Lasiter | G06F 3/0412 310/322 |
| 2015/0294663 | A1 * | 10/2015 | Klootwijk | C23C 16/45525 367/140 |
| 2016/0023244 | A1 | 1/2016 | Zhuang et al. | |
| 2016/0107194 | A1 | 4/2016 | Panchawagh et al. | |
| 2016/0153939 | A1 * | 6/2016 | Kato | B06B 1/0292 73/606 |
| 2016/0219375 | A1 * | 7/2016 | Hall | H04R 17/02 |
| 2016/0379973 | A1 * | 12/2016 | Rothberg | B06B 1/0292 438/53 |
| 2017/0069820 | A1 * | 3/2017 | Hada | H01L 41/29 |
| 2017/0110504 | A1 * | 4/2017 | Panchawagh | B06B 1/0207 |
| 2017/0170383 | A1 * | 6/2017 | Sammoura | G10K 11/32 |
| 2017/0258448 | A1 * | 9/2017 | Maruyama | G01S 7/52079 |
| 2017/0303897 | A1 * | 10/2017 | Rothberg | G01S 7/52084 |
| 2017/0333945 | A1 * | 11/2017 | Torashima | B06B 1/0292 |
| 2017/0365774 | A1 | 12/2017 | Rothberg et al. | |
| 2018/0221917 | A1 * | 8/2018 | Maruyama | G01N 29/221 |
| 2018/0257927 | A1 | 9/2018 | Rothberg et al. | |
| 2018/0312399 | A1 * | 11/2018 | Singh | B06B 1/0666 |
| 2018/0369862 | A1 | 12/2018 | Alie et al. | |
| 2019/0069842 | A1 | 3/2019 | Rothberg et al. | |
| 2019/0142387 | A1 | 5/2019 | Chen et al. | |
| 2019/0160490 | A1 | 5/2019 | Alie et al. | |
| 2019/0193116 | A1 * | 6/2019 | Horsley | G10K 9/122 |
| 2019/0231312 | A1 | 8/2019 | Fife et al. | |
| 2019/0261955 | A1 | 8/2019 | Chen et al. | |
| 2019/0275561 | A1 | 9/2019 | Fife et al. | |
| 2019/0299251 | A1 | 10/2019 | Chen et al. | |
| 2019/0336104 | A1 | 11/2019 | Fife et al. | |
| 2020/0041459 | A1 * | 2/2020 | Maruyama | B06B 1/0292 |
| 2020/0102214 | A1 | 4/2020 | Liu et al. | |
| 2020/0123005 | A1 * | 4/2020 | Sumida | B81C 1/00047 |
| 2020/0147641 | A1 | 5/2020 | Fife et al. | |
| 2020/0150252 | A1 | 5/2020 | Chen et al. | |

(56) References Cited

U.S. PATENT DOCUMENTS

| | | | |
|---|---|---|---|
| 2020/0156110 A1 | 5/2020 | Miao et al. | |
| 2020/0184176 A1 | 6/2020 | Liu et al. | |
| 2020/0184177 A1 | 6/2020 | Liu et al. | |
| 2020/0239299 A1 | 7/2020 | Liu et al. | |
| 2020/0254487 A1 | 8/2020 | Miao et al. | |
| 2020/0269279 A1 | 8/2020 | Miao et al. | |
| 2020/0269280 A1 | 8/2020 | Rothberg et al. | |
| 2020/0324318 A1 | 10/2020 | Liu et al. | |
| 2020/0324319 A1 | 10/2020 | Miao et al. | |
| 2020/0348794 A1 | 11/2020 | Ralston et al. | |
| 2020/0349342 A1 | 11/2020 | Ralston et al. | |
| 2021/0028792 A1 | 1/2021 | Hwang et al. | |
| 2021/0038193 A1 | 2/2021 | Liu et al. | |
| 2021/0088638 A1 | 3/2021 | Chen et al. | |
| 2021/0183832 A1 | 6/2021 | Chen et al. | |

FOREIGN PATENT DOCUMENTS

| | | | | |
|---|---|---|---|---|
| EP | 1761104 A1 | * | 3/2007 | ............ A61B 8/4483 |
| EP | 2508269 A2 | * | 10/2012 | ............ B06B 1/0292 |
| EP | 2792423 A2 | * | 10/2014 | ............ B06B 1/0292 |
| GB | 2436460 A | * | 9/2007 | ......... B81C 1/00158 |
| JP | 01-296122 A | | 11/1989 | |
| JP | 2014-212449 A | | 11/2014 | |
| JP | 2015103821 A | * | 6/2015 | |
| WO | WO-2005114820 A2 | * | 12/2005 | ............. A61B 10/00 |
| WO | WO-2010100861 A1 | * | 9/2010 | ......... B81C 1/00476 |
| WO | WO-2010109205 A2 | * | 9/2010 | ............ B06B 1/0292 |
| WO | WO-2014080310 A2 | * | 5/2014 | ............ C23C 16/56 |
| WO | WO 2016/007250 A1 | | 1/2016 | |
| WO | WO 2016/106153 A1 | | 6/2016 | |

OTHER PUBLICATIONS

Wygant, Ira O., Mario Kupnik, and Butrus T. Khuri-Yakub. "An analytical model for capacitive pressure transducers with circular geometry." Journal of Microelectromechanical Systems 27.3 (2018): 448-456. (Year: 2018).*

Invitation to Pay Additional Fees mailed Jul. 3, 2019 in connection with International Application No. PCT/US2019/030388.

International Preliminary Report on Patentability mailed Nov. 12, 2020 in connection with International Application No. PCT/US2019/030388.

International Search Report and Written Opinion mailed Aug. 27, 2019 in connection with International Application No. PCT/US2019/030388.

Daft et al., Microfabricated ultrasonic transducers monolithically integrated with high voltage electronics. Proc Ultrason Symp. 2004;493-6.

Gurun et al., Front-end CMOS electronics for monolithic integration with CMUT arrays: circuit design and initial experimental results. Proc Ultrason Symp. 2008;390-3.

Kuntzman et al., Rotational Capacitive Micromachined Ultrasonic Transducers (cMUTs). Journal of Microelectromechnaical Systems. Feb. 2014; 23(1): 1-3.

Kupnik et al., CMUT Fabrication Based On A Thick Buried Oxide Layer. Proc IEEE Ultrason Symp. Oct. 2010; 2010:547-550. doi:10.1109/ULTSYM.2010.5935935. Epub Jun. 8, 2012. 10 pages.

Kupnik et al., Wafer-Bonded CMUT Meets CMOS. 2010 CMOS Emerging Technology Workshop. May 2010 21;1-22.

PCT/US2019/030388, Nov. 12, 2020, International Preliminary Report on Patentability.

PCT/US2019/030388, Aug. 27, 2019, International Search Report and Written Opinion.

PCT/US2019/030388, Jul. 3, 2019, Invitation to Pay Additional Fees.

Extended European Search Report for European Application No. 19795861.4, dated Dec. 20, 2021.

Notice of Reasons for Refusal issued in corresponding Japanese Application No. 2020-560488 mailed May 8, 2023 (17 pages).

* cited by examiner

PRESSURE PORT FOR ULTRASONIC TRANSDUCER ON CMOS SENSOR

CROSS-REFERENCE TO RELATED APPLICATIONS

The present application claims the benefit under 35 U.S.C. § 119(e) of U.S. Patent Application Ser. No. 62/666,556, filed May 3, 2018, and entitled "PRESSURE PORT FOR ULTRASONIC TRANSDUCER ON CMOS SENSOR," which is hereby incorporated herein by reference in its entirety.

The present application claims the benefit under 35 U.S.C. § 119(e) of U.S. Patent Application Ser. No. 62/696,305, filed Jul. 10, 2018, and entitled "PRESSURE PORT FOR ULTRASONIC TRANSDUCER ON CMOS SENSOR," which is hereby incorporated herein by reference in its entirety.

BACKGROUND

Field

The present application relates to micromachined ultrasonic transducers.

Related Art

Some micromachined ultrasonic transducers include a flexible membrane suspended above a substrate. A cavity is located between part of the substrate and the membrane, such that the combination of the substrate, cavity, and membrane form a variable capacitor. If actuated, the membrane may generate an ultrasound signal. In response to receiving an ultrasound signal, the membrane may vibrate, resulting in an output electrical signal.

BRIEF SUMMARY

Pressure ports for micromachined ultrasonic transducers are described.

BRIEF DESCRIPTION OF DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

DETAILED DESCRIPTION

Aspects of the present application provide a micromachined ultrasonic transducer (MUT) comprising a pressure port. The MUT may include a sealed cavity, for example sealed on a top and bottom side by a membrane and a substrate, respectively. The pressure port may represent an access hole to the sealed cavity. The pressure port may function to control the pressure within the sealed cavity during manufacture of the MUT. Once the pressure of the cavity, or cavities, is set as desired, the pressure port may be sealed.

The inclusion of a pressure port for a MUT may provide various benefits. The pressure port may allow for control of the pressure of the sealed cavity of the MUT. Some ultrasound devices comprise large numbers of MUTs, such as hundreds, thousands, or hundreds of thousands of MUTs. Operation of such ultrasound devices may benefit in terms of accuracy and dynamic range (e.g., by minimizing damping) from having a substantially equal or uniform pressure across the area of the MUTs. Thus, providing pressure ports for individual MUTs or sub-groups of MUTs of the ultrasound device may facilitate achieving more uniform pressure across the sensing area. The pressure ports may allow for equalization of cavity pressure over a sensing area comprising multiple MUTs. The pressure ports may be used during manufacture, and sealed after the cavities are equalized in terms of pressure.

Various characteristics of ultrasonic transducer pressure ports may be selected according to aspects of the present application. According to some aspects, each ultrasonic transducer may have one or more respective pressure ports. According to alternative aspects, a pressure port may be shared by two or more ultrasonic transducers. According to an aspect of the present application, an array of ultrasonic transducer may include respective pressure ports oriented at a same angle as each other relative to the array. According to alternative aspects, an array of ultrasonic transducers may include respective pressure ports, in which two or more of the pressure ports are oriented at different angles relative to the array. The number of pressure ports provided for an array of ultrasonic transducers may be less than, equal to, or greater than the number of ultrasonic transducers. Further variations are possible.

The aspects and embodiments described above, as well as additional aspects and embodiments, are described further below. These aspects and/or embodiments may be used individually, all together, or in any combination of two or more, as the application is not limited in this respect.

Figure 1:
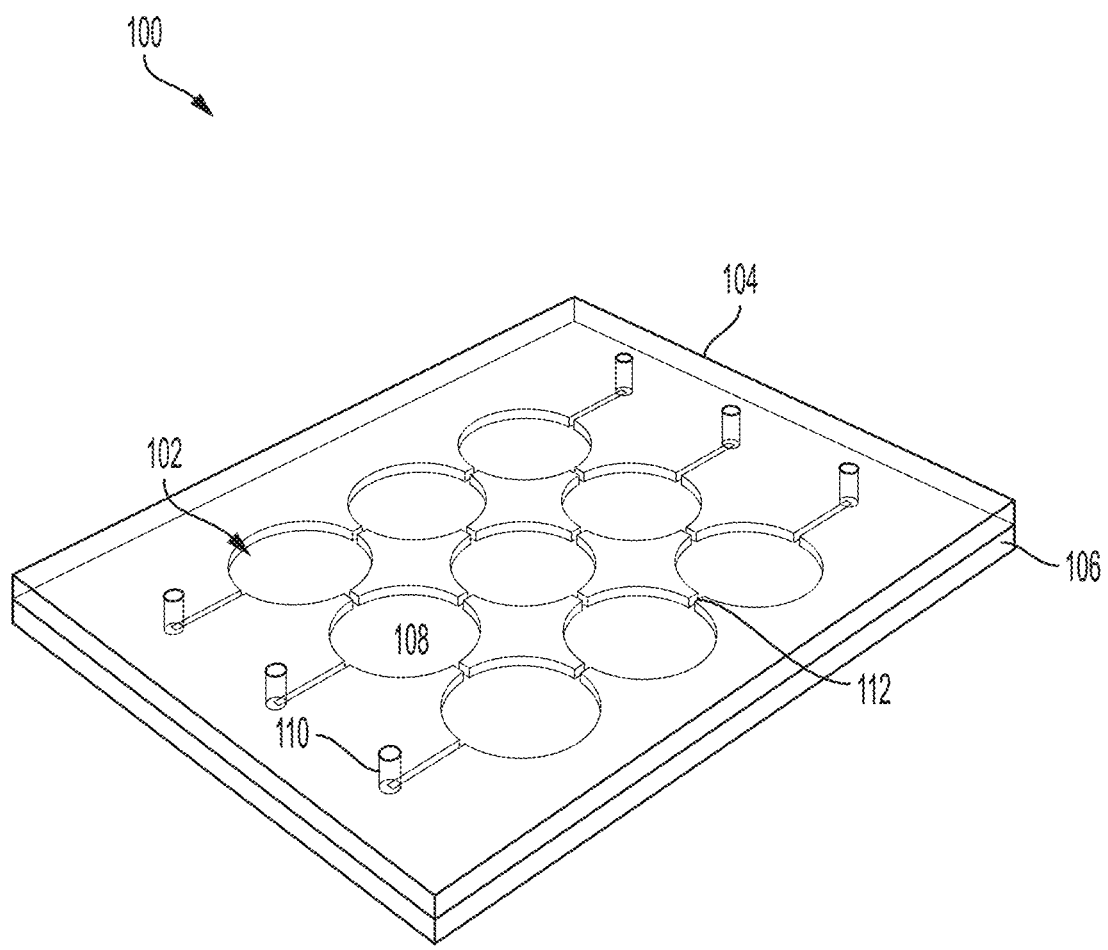
FIG. 1 is a perspective view of an array of micromachined ultrasonic transducers comprising pressure ports for access to cavities of the micromachined ultrasonic transducer.

According to an aspect of the present application, pressure ports are provided for an array of ultrasonic transducers. In some embodiments, the ultrasonic transducers include sealed cavities connected to each other by interconnection channels, and a plurality of pressure ports are shared by the array of ultrasonic transducers. FIG. 1 is a non-limiting example, and is a perspective view of an array of micromachined ultrasonic transducers comprising pressure ports for access to cavities of the micromachined ultrasonic transducer. The ultrasound device 100 comprises an array of nine MUTs 102, formed by a membrane 104, insulating layer 106, and cavities 108. Pressure ports 110 are provided, and channels 112 interconnect the cavities 108. In some embodiments, insulating layer 106 may be a part of a complementary metal-oxide-semiconductor (CMOS) wafer, and cavities 108 can be formed in insulating layer 106 of the CMOS wafer.

The pressure ports 110 may have any suitable location. In the illustrated non-limiting example, they are positioned at the periphery of the array, and in this non-limiting example on two opposite side of the periphery of the array. When the pressure ports are disposed at the periphery of the array, as shown, control over the cavity pressure of the cavities internal to the array may still be achieved because of the presence of channels 112, which may be air channels. However, alternative configurations are possible. For example, a pressure port may be provided for each individual cavity as shown in other embodiments. Alternatively, fewer pressure ports may be provided than shown, with additional channels 112 provided to allow for control of the cavity pressure across the array.

Various characteristics of the pressure ports 110 may be noted, including positioning and size. In the non-limiting example shown, the pressure ports 110 are positioned on two opposite sides of the array. In this non-limiting example, two pressure ports are positioned on a line bisecting the ultrasonic transducers in a given row. However, alternative positioning of pressure ports is possible. The pressure ports may have any suitable dimensions and may be formed in any suitable manner. In some embodiments, the pressure ports are sufficiently small to not have a negative impact on the performance of the ultrasonic transducers. Also, the pressure ports may be sufficiently small to allow them to be sealed once the pressures of cavities 108 are set to a desired value. For example, the pressure ports may have diameters between approximately 0.1 microns and 20 microns, including any value or range of values within that range. The pressure ports may be sealed in any suitable manner, such as with a metal material. For example, aluminum may be sputtered to seal the pressure ports.

The pressure ports may be created and used during manufacture of the MUT(s). In some embodiments, the sealed cavities may be formed using a wafer bonding technique. The wafer bonding technique may be inadequate for achieving uniform cavity pressure across a wafer or array of MUTs. Also, the chemicals present for wafer bonding may unequally occupy or remain in certain cavities of an array of MUTs. After the cavities are sealed (for example, by the wafer bonding), the pressure ports may be opened. The pressures of the sealed cavities may then be equalized, or made substantially equal, through exposure of the wafer to a desired, controlled pressure. Also, desired chemicals (e.g., Argon) may be introduced to the cavities through the pressure ports. Subsequently, the pressure ports may be sealed.

Thus, the inventors have appreciated that control of the pressure and/or chemical content of the sealed cavities of a plurality of MUTs may be improved through use of a pressure port. The pressure port may provide greater control over these parameters than the wafer bonding process used for forming the sealed cavities.

Figure 2:
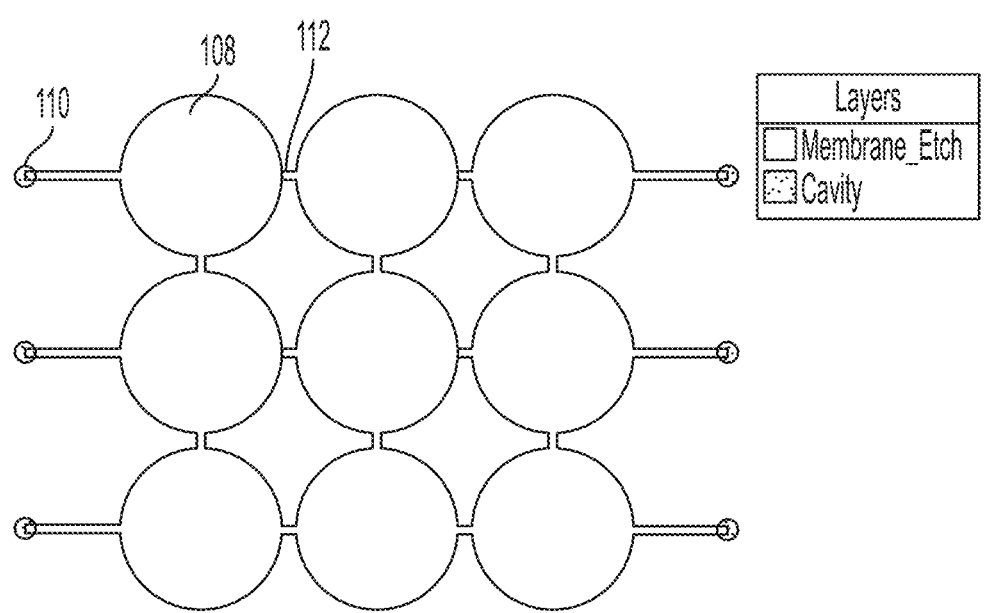
FIG. 2 is a schematic top view of the cavity layer of the structure of FIG. 1.

FIG. 2 illustrates a top view of the cavity layer of the ultrasound device 100 of FIG. 1. As shown, nine cavities are included, interconnected by channels 112. Again, the channels 112 may be air channels, allowing pressure in the adjoining cavities to be set at a uniform level. The channels 112 may have any suitable dimensions for this purpose, such as being between 0.1 microns and 20 microns, including any value or range of values within that range.

The ultrasound device of FIGS. 1 and 2 is a non-limiting example. The number of micromachined ultrasonic transducers shown, the shape, dimensions, and positioning are all variables. For example, FIG. 2 illustrates circular cavities, but other shapes are possible, such as polygonal, square, or any other suitable shape. The positioning and number of pressure ports shown may also be selected for a particular application.

Figure 3:
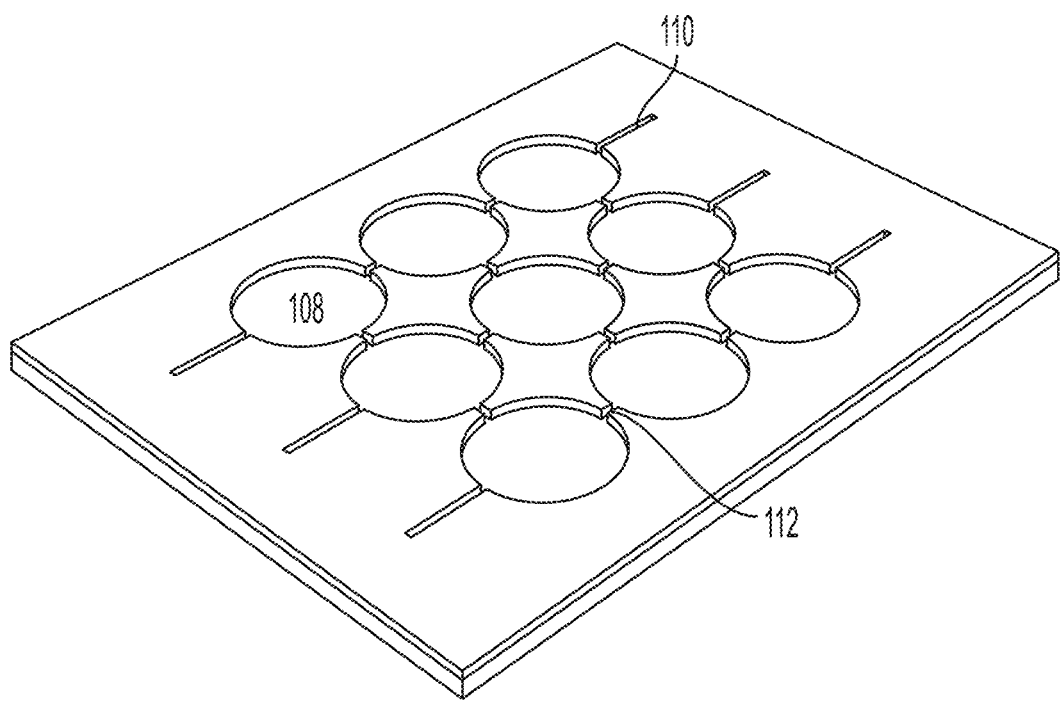
FIG. 3 illustrates a layer of the device of FIG. 1 including cavities and channels.

FIG. 3 illustrates a perspective view of the cavity layer of the device of FIG. 1 including cavities and channels. In this figure, the membrane layer of the ultrasound device 100 is omitted. The cavities 108, channels 112, and part of the pressure ports 110 may be formed, for example by etching. Subsequently, the membrane 104 may be formed to seal the cavities 108 by creating a membrane layer. A vertical part of the pressure ports 110 may then be etched through the membrane 104 to form the ultrasound device 100.

Figure 4:
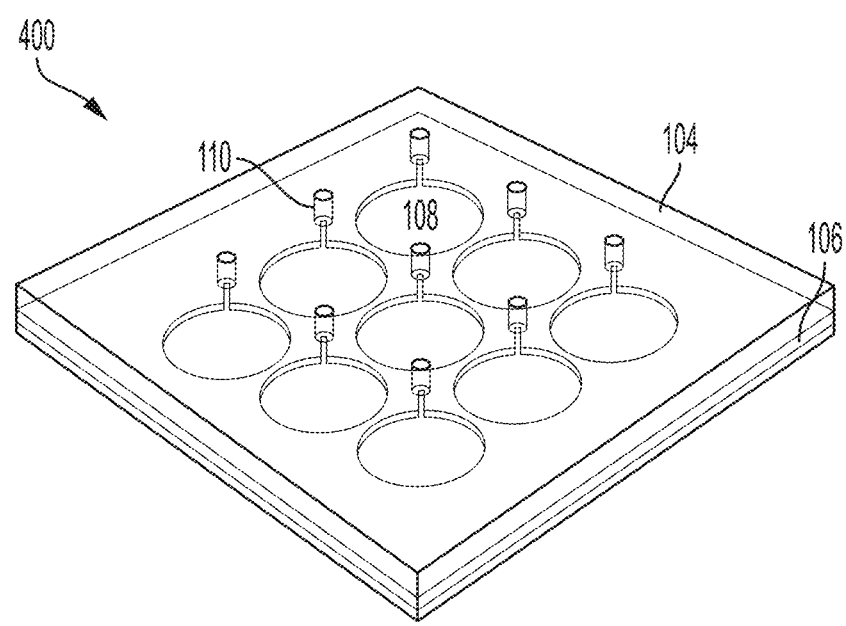
FIG. 4 illustrates an alternative to FIG. 1 having an array of ultrasonic transducers with respective pressure ports.

As described previously, the number and positioning of pressure ports provided with an array of ultrasonic transducers may be different than that shown in FIG. 1. According to an aspect of the present application, an array of ultrasonic transducers comprises an array of cavities with respective pressure ports. FIG. 4 illustrates an example, representing an alternative to FIG. 1 and having an array of ultrasonic transducers with respective pressure ports. The ultrasound device 400 includes the cavities 108, membrane 104, and insulating layer 106. One pressure port is provided for each cavity 108 in this non-limiting embodiment. In addition, the cavities are not interconnected by channels 112. Also, in this non-limiting example it is seen that the pressure ports are all oriented at a common angle relative to the cavities, and are not all disposed at a periphery of the cavity array.

Figure 5:
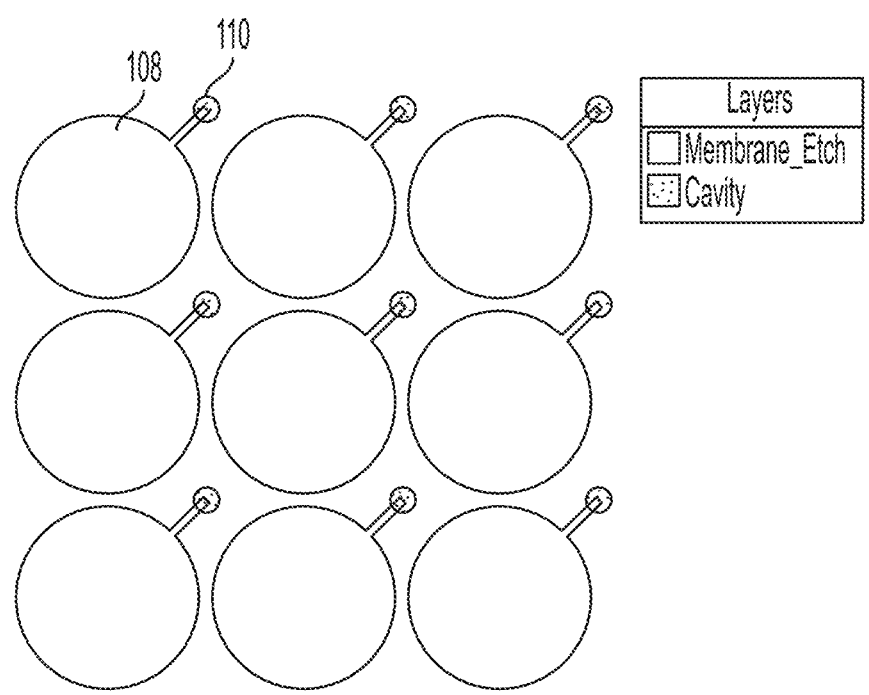
FIG. 5 is a schematic top view of the cavity layer of the structure of FIG. 4.

FIG. 5 is a schematic top view of the cavity layer of the structure of FIG. 4. As shown, the cavities 108 include pressure ports 110 which include both a portion in-plane with the cavities and a portion perpendicular to the cavities (represented by the circles at the end of the portion in-plane with the cavities).

Figure 6:
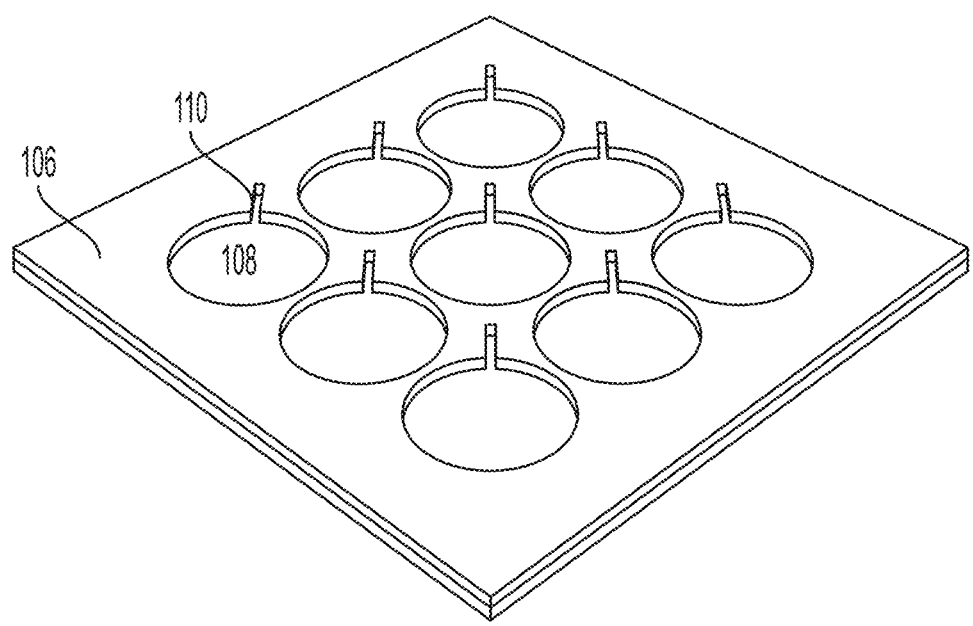
FIG. 6 illustrates the cavity layer of FIG. 4 including cavities and portions of the pressure ports.

FIG. 6 illustrates the cavity layer of FIG. 4 including cavities 108 and pressure ports 110. In this view, the portion of the pressure ports in-plane with the cavities is illustrated. The portion of the pressure portions extending upward, perpendicular to the cavities 108 is not shown since that portion extends through the membrane 104, which is not part of FIG. 6. The cavities 108 and portions of the pressure ports 110 in-plane with the cavities 108 may be formed in any suitable manner. For example, any suitable technique for etching the insulating layer 106 may be used to form the cavities 108 and in-plane portions of the pressure ports 110. The ultrasound device 400 of FIG. 4 may be formed from the structure of FIG. 6 by forming the membrane 104 and etching vertical portions of the pressure ports 110.

Figure 7:
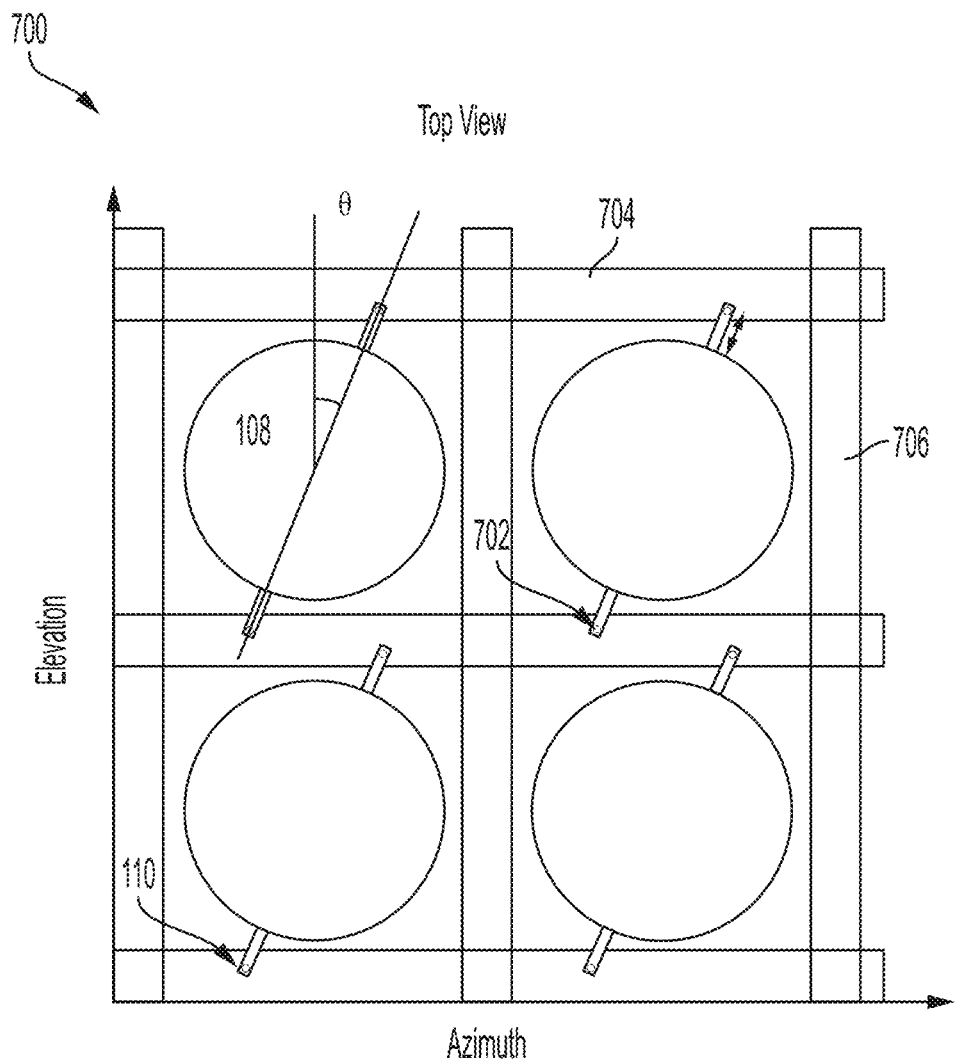
FIG. 7 illustrates an alternative array of ultrasonic transducers and pressure ports comprising two pressure ports per ultrasonic transducer.

As described previously, various configurations of pressure ports may be used with an array of ultrasonic transducers. FIGS. 1 and 4 illustrate two non-limiting examples. FIG. 7 illustrates a further alternative. In the non-limiting example of FIG. 7, two pressure ports are provided for each cavity. Providing more than one pressure port per cavity may make it easier to remove undesirable elements from the cavity, such as water or other elements. Having more than one port per cavity may also facilitate achieving a desired pressure for the cavity. In the ultrasound device 700, the pressure ports are represented by the channels, or extensions, with the openings 702 at the end. It can be seen that the pressure ports 110 are oriented at an angle θ with respect to the elevation direction. That angle may be between 5 degrees and 40 degrees, or any other suitable number. Also shown in FIG. 7 are metal lines 704 and 706. Metal lines 704 run in the azimuth direction, while metal lines 706 run in the elevation direction. The metal lines 704 and 706 may represent conductive traces for providing signals to/from the ultrasonic transducers. In some embodiments, it may be preferable to have all the pressure ports terminate on metal lines oriented in only the azimuth or elevation direction, and thus angling the pressure ports at the angle θ may facilitate such a configuration. For instance, as shown, all the pressure ports in FIG. 7 terminate at metal lines oriented in the azimuth direction. The metal of the metal lines may seal the ends of the pressure ports. For example, sputtering aluminum to form the metal lines may seal the pressure ports.

Figure 8:
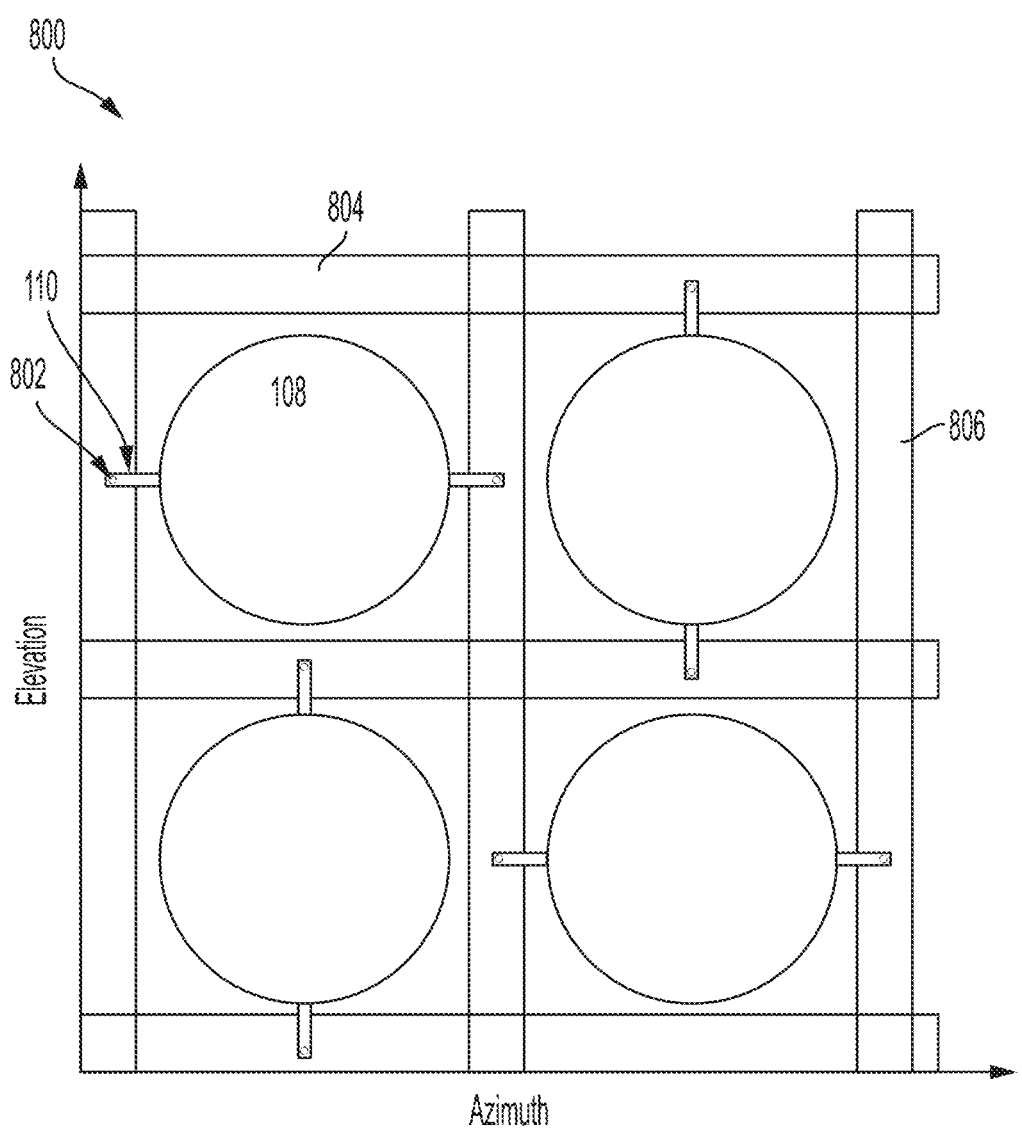
FIG. 8 illustrates an alternative array of ultrasonic transducers and pressure ports comprising two pressure ports per ultrasonic transducer.

FIG. 8 illustrates an alternative array of ultrasonic transducers and pressure ports comprising two pressure ports per ultrasonic transducer. The illustrated ultrasound device 800 differs from that of FIG. 7 in that the pressure ports for neighboring cavities are oriented differently than each other. In this example, when the pressure ports for a given cavity are oriented along the azimuth direction, the pressure ports for its immediately neighboring cavities are oriented along the elevation direction, and vice versa.

Figure 9:
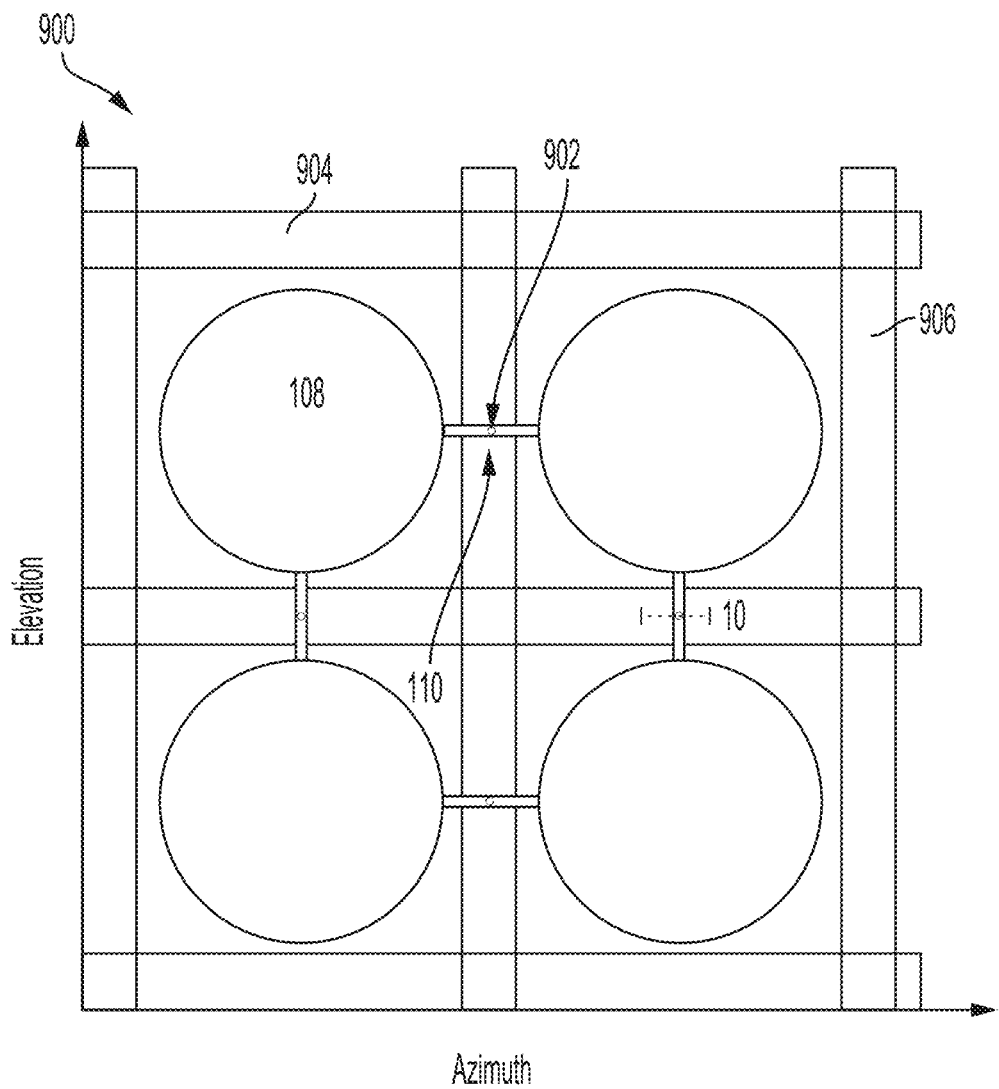
FIG. 9 illustrates an alternative array of ultrasonic transducers and pressure ports in which the pressure ports are shared among the ultrasonic transducers.

FIG. 9 illustrates an alternative array of ultrasonic transducers and pressure ports in which the pressure ports are shared among the ultrasonic transducers. The ultrasound device 900 includes cavities 108, metal lines 904 and 906, channels 110 and access holes 902. The pressure ports may represent a combination of channels 110 and access holes 902. The access holes may extend vertically, for example perpendicular to the cavities 108, as shown in FIG. 9 as openings 902. The channels 110 may interconnect neighboring cavities 108 as shown. In this example, the same number of pressure ports and cavities are provided and the pressure ports are accessible internal to the array as opposed to being disposed at a periphery of the array.

Figure 10:
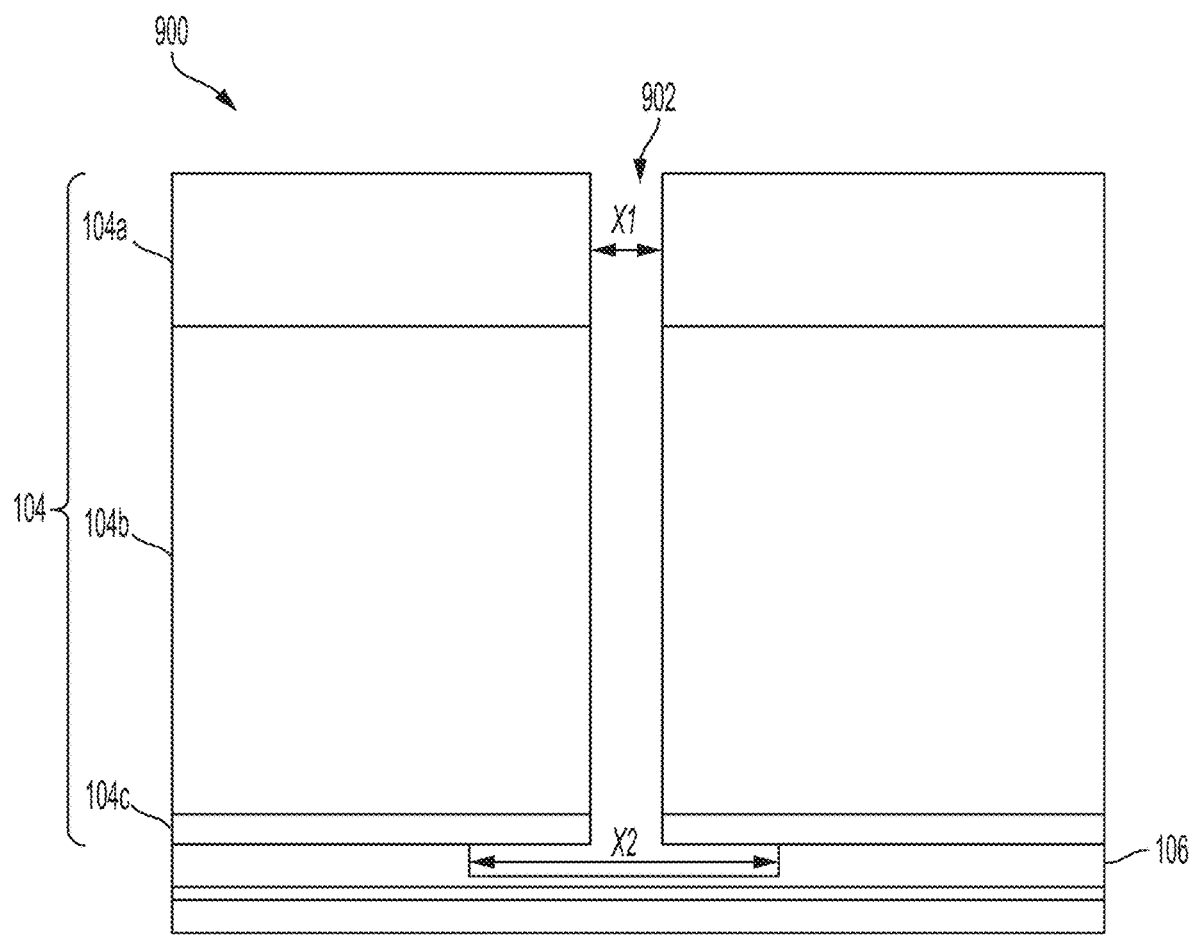
FIG. 10 is a cross-sectional view of a pressure port of a type which may be used in the device of FIG. 9.

FIG. 10 is a cross-sectional view 10 of a pressure port of a type which may be used in the device of FIG. 9. The pressure port includes a vertical portion represented by 902, having a width X1, and an in-plane portion, or channel, with a width X2. The value of X1 may be selected so as to be sufficiently small to not negatively impact operation of the ultrasonic transducer, and also to be sufficiently small to allow easy filling. In some embodiments, X1 may assume any of the value described previously herein with respect to pressure port and access hole dimensions, such as being between 0.1 microns and 20 microns. The value of X2 may likewise assume any such value. In the illustrated example, X1 is less than X2.

In some embodiments, membrane 104 may be formed of one or more layers with different material compositions. Membrane 104 may be formed from a silicon on insulator (SOI) wafer. The SOI wafer may comprise several layers, including but not limited to a buried oxide (BOX) layer 104a, a single crystalline layer 104b, and a thermal oxide layer 104c. The SOI wafer may further comprise a handling wafer, which is removed after wafer bonding by any suitable technique such as chemical-mechanical polishing (CMP). BOX layer 104a may be any suitable thickness, such as being between 0.5 and 2 microns thick or any other suitable value. Single crystalline layer 104b may be single crystalline Si or any suitable single crystalline material. Single crystalline layer 104b may also be any suitable thickness to enable operation of the MUTs, including being between 4 and 10 microns thick. Thermal oxide layer 104c may be any suitable thickness, such as being between 100 and 300 nm thick.

Figure 11:
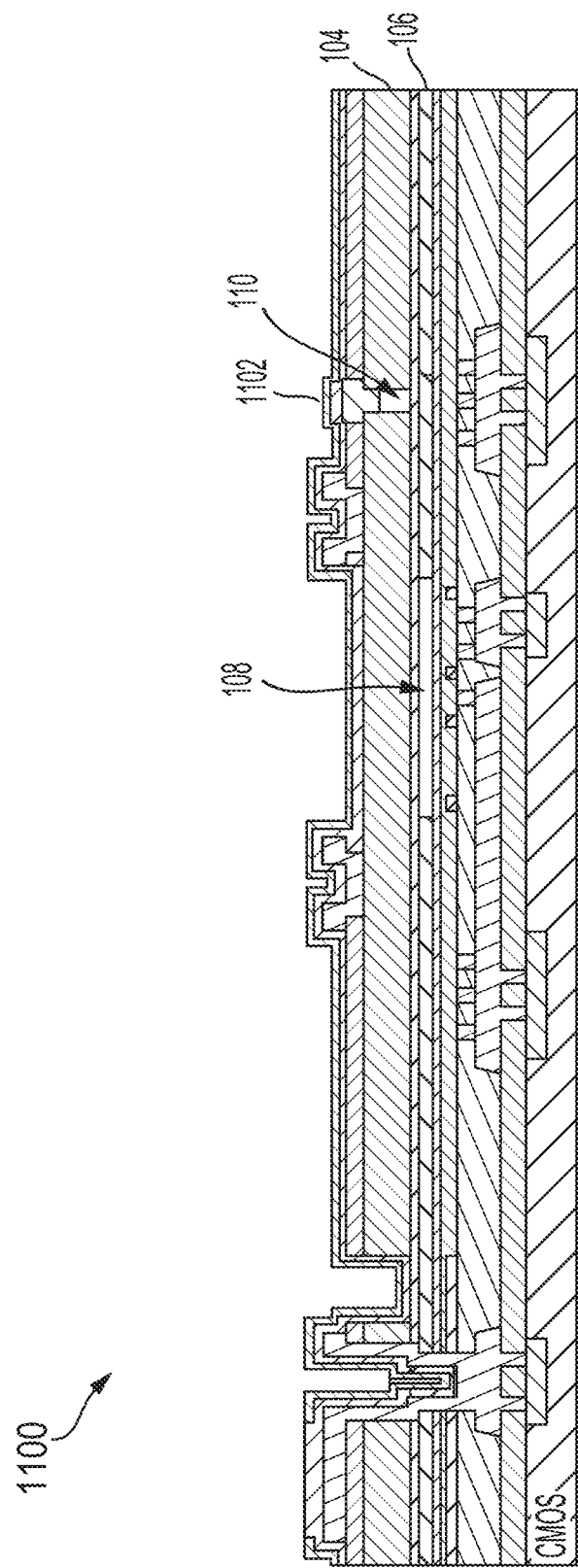
FIG. 11 is a cross-sectional view of a non-limiting example of a micromachined ultrasonic transducer having a pressure port.

FIG. 11 is a cross-sectional view of a non-limiting example of a MUT 1100 having a cavity 108 and pressure port 110. As shown, the pressure port may be sealed, and thus the illustrated device may represent the state of the device after the cavity pressure has been set to a desired value. At that point, the pressure port may be sealed with seal 1102 to provide a substantially constant pressure within the sealed cavity as a function of time.

Figure 12:
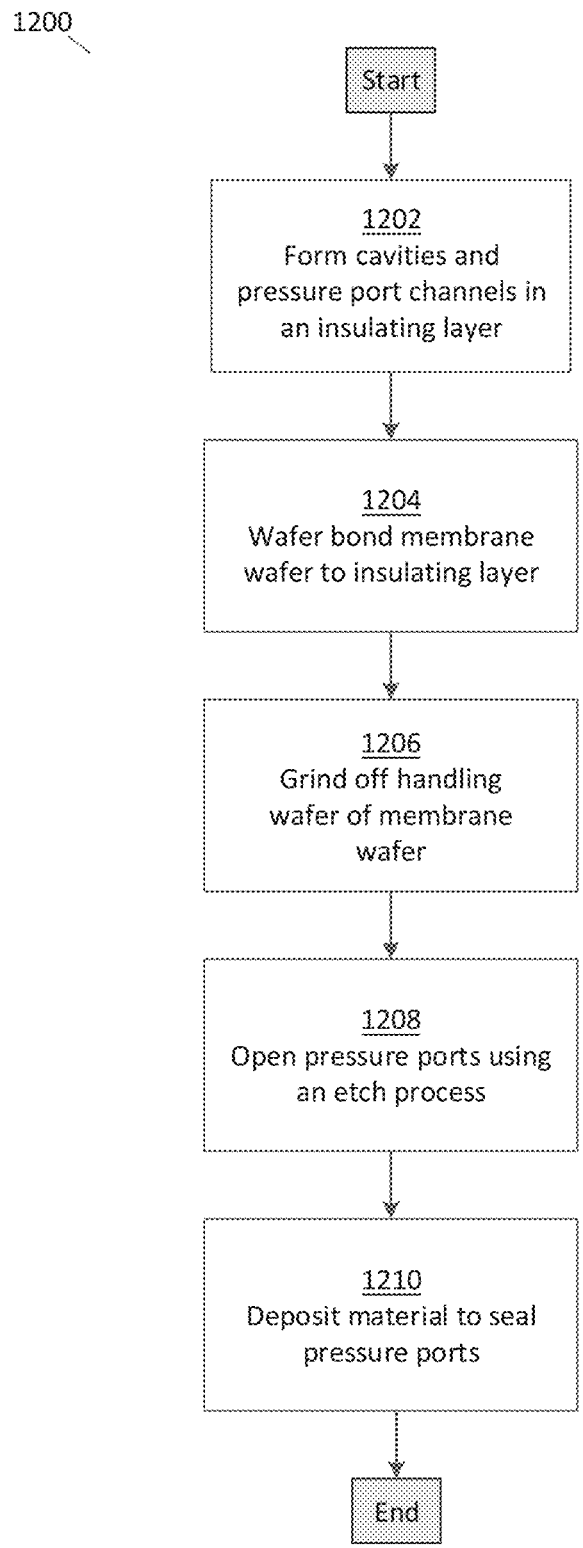
FIG. 12 is a flowchart of a fabrication process for forming an ultrasonic transducer having a pressure port, according to some embodiments.

The fabrication process of a MUT like MUT 1100 is described by process 1200 of FIG. 12. First, in act 1202, features such as but not limited to cavities 108, pressure ports 110, and/or channels 112 are formed in insulating layer 106. Cavities 108, pressure ports 110, and/or channels 112 may be formed by any suitable etch process including reactive ion etching (RIE), deep reactive ion etching (DRIE), ion milling, plasma etching, or any other suitable method. Insulating layer 106 may be a part of a larger CMOS wafer such that the cavities are electrically coupled to other elements of the CMOS wafer.

In act 1204, the insulating layer 106 with features may be wafer bonded to a membrane wafer, which may be an SOI wafer of the type discussed previously. The wafer bonding process may be a low temperature wafer bonding process. The wafer bonding process may also include a post-process annealing step. During annealing, gettering materials may be present to help control the pressure inside the cavities 108. For example, gettering materials might include Ti, TiN, SrO, and/or Zr—Al. In act 1206, the handling wafer of the membrane wafer may be ground off, allowing the membrane 104 above the cavities 108 to flex. The handling wafer may be ground off in any suitable way including chemical-mechanical polishing.

In act 1208, openings such as openings 902 are formed to open pressure ports 110, allowing the pressure of the cavities 108 to equalize. Openings may be formed using any suitable etch process such as RIE and/or DRIE. In some embodiments, RIE is first used to etch through BOX layer 104a. Then, DRIE is used to etch single crystalline layer 104b, and RIE is again used to etch through thermal oxide layer 104c. Since the pressure ports 110 are opened under vacuum, any outgassed materials from the wafer bonding and/or annealing processes escape during act 1208, and the pressure of the cavities 108 equalizes to that of the vacuum chamber.

In act 1210, the pressure ports 110 are sealed so that the cavities 108 may remain at a suitable pressure for operation. The pressure ports 110 may be sealed by any suitable material, or by any suitable process such as but not limited to a sputtering process. The pressure ports 110 may be sealed by a multilayered structure formed of multiple materials. Example materials include Al, Cu, Al/Cu alloys, and TiN in any suitable combination.

The micromachined ultrasonic transducers described herein may be of various types. In some embodiments, they may be capacitive micromachined ultrasonic transducers (CMUTs). In such situations, they may be formed by wafer bonding or sacrificial release methods. In some embodiments, the micromachined ultrasonic transducers are piezoelectric micromachined ultrasonic transducers (PMUTs).

Various types of ultrasound devices may implement MUTs with pressure ports of the types described herein. In some embodiments, a handheld ultrasound probe may include an ultrasound-on-a-chip comprising MUTs with pressure ports. In some embodiments, an ultrasound patch may implement the technology. A pill may also utilize the technology. Thus, aspects of the present application provide for such ultrasound devices to include MUTs with pressure ports.

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described.

As described, some aspects may be embodied as one or more methods. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements.

As used herein, the term "between" used in a numerical context is to be inclusive unless indicated otherwise. For example, "between A and B" includes A and B unless indicated otherwise.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

The invention claimed is:

1. An ultrasound device, comprising:
an array of capacitive micromachined ultrasonic transducers including a plurality of capacitive micromachined ultrasonic transducers having respective sealed cavities between a substrate and a membrane, the plurality of capacitive micromachined ultrasonic transducers comprising thousands of capacitive micromachined ultrasonic transducers;
a plurality of pressure ports extending through the membrane and configured to provide access to the respective sealed cavities of the plurality of capacitive micromachined ultrasonic transducers to control a pressure of the sealed cavities; and
conductive traces formed in metal lines that separate the plurality of capacitive micromachined ultrasonic transducers,
wherein the plurality of pressure ports are shared commonly by the plurality of capacitive micromachined ultrasonic transducers,
wherein each pressure port of the plurality of pressure ports comprises a portion in-plane with the plurality of sealed cavities and a portion substantially perpendicular to the plurality of sealed cavities,
wherein each pressure port of the plurality of pressure ports is sealed at one end by one of the metal lines of the conductive traces, and
wherein adjacent pressure ports of the plurality of pressure port are sealed by different metal lines of the conductive traces.

2. The ultrasound device of claim 1, wherein the substrate is bonded with an integrated circuit substrate comprising integrated circuitry.

3. The ultrasound device of claim 1, wherein the substrate comprises integrated circuitry.

4. The ultrasound device of claim 1, wherein a first pressure port of the plurality of pressure ports is substantially free of solid material.

5. The ultrasound device of claim 1, wherein a first pressure port of the plurality of pressure ports comprises a void.

6. The ultrasound device of claim 5, wherein the void is filled with a gas.

7. The ultrasound device of claim 1, wherein a first pressure port of the plurality of pressure ports projects substantially perpendicular to a long axis of a sealed cavity of the respective sealed cavities.

8. The ultrasound device of claim 1, wherein a first pressure port of the plurality of pressure ports comprises a turn.

9. The ultrasound device of claim 8, wherein the first pressure port comprises a 90-degree turn.

10. The ultrasound device of claim 1, wherein a first pressure port of the plurality of pressure ports comprises a bend.

11. A capacitive micromachined ultrasonic transducer, comprising:
an array of thousands of capacitive micromachined ultrasonic transducers, having an array of sealed cavities, the array of sealed cavities comprising thousands of sealed cavities;
a plurality of pressure ports configured to control a pressure of the respective sealed cavities of the array of sealed cavities, wherein the plurality of pressure ports are shared commonly by the array of sealed cavities; and
conductive traces formed in metal lines that separate the array of sealed cavities in a plan view,
wherein each pressure port of the plurality of pressure ports comprises a portion in-plane with the plurality of sealed cavities and a portion substantially perpendicular to the array of sealed cavities,
wherein each pressure port of the plurality of pressure ports is sealed at one end by one of the metal lines of the conductive traces, and
wherein adjacent pressure ports of the plurality of pressure port are sealed by different metal lines of the conductive traces.

12. The capacitive micromachined ultrasonic transducer of claim 11, wherein a first pressure port of the plurality of pressure ports comprises an in-plane portion and a substantially perpendicular portion, and wherein the substantially perpendicular portion is thinner than the in-plane portion.

13. The capacitive micromachined ultrasonic transducer of claim 11, wherein a first pressure port of the plurality of pressure ports is part of a channel interconnecting two sealed cavities of the array of sealed cavities.

14. The capacitive micromachined ultrasonic transducer of claim 11, wherein a first pressure port of the plurality of pressure ports comprises a 90-degree bend.

15. The capacitive micromachined ultrasonic transducer of claim 11, wherein a first pressure port of the plurality of pressure ports is sealed by a metal.

16. The capacitive micromachined ultrasonic transducer of claim 11, wherein the capacitive micromachined ultrasonic transducer is disposed in a handheld ultrasound probe.

\* \* \* \* \*